(12) United States Patent
Voor, Jr.

(10) Patent No.: US 9,335,303 B2
(45) Date of Patent: May 10, 2016

(54) ULTRASONIC SCANNING FIXTURE ASSEMBLY

(71) Applicant: Sikorsky Aircraft Corporation, Stratford, CT (US)

(72) Inventor: James A. Voor, Jr., Thomaston, CT (US)

(73) Assignee: SIKORSKY AIRCRAFT CORPORATION, Stratford, CT (US)

(*) Notice: Subject to any disclaimer, the term of this patent is extended or adjusted under 35 U.S.C. 154(b) by 302 days.

(21) Appl. No.: 14/047,048

(22) Filed: Oct. 7, 2013

(65) Prior Publication Data

US 2015/0096382 A1    Apr. 9, 2015

(51) Int. Cl.
*G01N 29/04*  (2006.01)
*G01N 29/26*  (2006.01)
*G01N 29/22*  (2006.01)

(52) U.S. Cl.
CPC .............. *G01N 29/26* (2013.01); *G01N 29/225* (2013.01)

(58) Field of Classification Search
CPC . G01N 29/26; G01N 29/043; G01N 29/0645; G01N 29/22; G01N 29/265; G01N 29/28; G01N 29/225; G01N 29/275; G01N 29/223; G01N 29/226
USPC .............. 73/618, 622, 633, 634, 640, 649
See application file for complete search history.

(56) References Cited

U.S. PATENT DOCUMENTS

| | | | | |
|---|---|---|---|---|
| 3,837,202 A * | 9/1974 | Hetherington | .......... | B21C 51/00 73/640 |
| 4,404,853 A * | 9/1983 | Livingston | ............ | E21B 17/006 73/622 |
| 4,843,884 A * | 7/1989 | House | .................... | G01N 29/26 73/622 |
| 5,007,291 A * | 4/1991 | Walters | ................ | G01N 29/043 73/640 |
| 5,066,452 A * | 11/1991 | Hancock | ................ | G21C 17/06 376/240 |
| 5,585,565 A * | 12/1996 | Glascock | ............... | G01B 17/02 73/622 |
| 5,600,069 A * | 2/1997 | Girndt | .................. | G01N 29/225 73/622 |
| 5,698,787 A | 12/1997 | Parzuchowski et al. | | |
| 6,748,808 B2 * | 6/2004 | Lam | .................... | G01N 29/0609 73/622 |
| 6,945,113 B2 * | 9/2005 | Siverling | ............. | G01N 29/275 73/622 |
| 7,249,512 B2 * | 7/2007 | Kennedy | .............. | G01N 29/225 73/618 |
| 7,337,673 B2 | 3/2008 | Kennedy et al. | | |
| 7,430,913 B2 * | 10/2008 | Sarr | ...................... | G01N 29/225 73/618 |
| 7,464,596 B2 * | 12/2008 | Bui | ...................... | G01N 29/043 73/618 |
| 8,091,423 B2 * | 1/2012 | Zimmerman | ........ | G01N 29/043 73/588 |
| 8,347,746 B2 | 1/2013 | Hafenrichter et al. | | |

* cited by examiner

*Primary Examiner* — Helen Kwok
(74) *Attorney, Agent, or Firm* — Cantor Colburn LLP

(57) ABSTRACT

An apparatus for use in scanning a material includes a top member having a first body with a first plurality of holes; a bottom member having a second body with a second plurality of holes; and an interconnecting member connecting the top member and the second member to provide a gap between the top member and the bottom member. Each hole in the top member is aligned with a corresponding hole in the bottom member to form a hole-pair.

18 Claims, 3 Drawing Sheets

ULTRASONIC SCANNING FIXTURE ASSEMBLY

BACKGROUND

The subject matter disclosed herein relates generally to the field of non-destructive inspection and, more particularly, to the use of a portable hand-held scanning fixture assembly for through-transmission ultrasonic inspection of a composite structure.

DESCRIPTION OF RELATED ART

Typically, non-destructive inspection of a composite structure must be made to detect any type of damage occurring anywhere on or within the composite structure including but not limited to delamination, erosion, impact damage, water ingression, disbands, inclusions, porosity, and cracking. In rotor blades such as, e.g., a rotor blade on a rotorcraft, these defects, if undetected, may result in a significant loss of strength in the rotor blade that may compromise its integrity. For example, non-destructive inspection of a rotor blade may include various types of sensors/transducers to perform non-destructive testing including pulse-echo, through-transmission, or shear wave testing may be utilized. For example, through-transmission ultrasonic inspection may require that a trained technician manually hold two transducers against each surface of the rotor blade and move the transducers along the blade to ensure that all desired portions of the rotor blade are tested. The transducers must be perfectly aligned co-axially in order to provide an accurate measurement of the rotor blade. Misalignment of the transducers may indicate delamination or disbanding within the rotor blade when the rotor blade may be free of such defects. Manual manipulation of the transducers for co-axial alignment is extremely difficult and time consuming. An improved hand-held scanning fixture assembly for manual through-transmission and pulse echo ultrasonic inspection would be well received in the field.

BRIEF SUMMARY OF THE INVENTION

According to an aspect of the invention, an apparatus for use in scanning a material includes a top member having a first body with a first plurality of holes; a bottom member having a second body with a second plurality of holes; and an interconnecting member connecting the top member and the second member to provide a gap between the top member and the bottom member, where each hole in the top member is aligned with a corresponding hole in the bottom member.

According to another aspect of the invention, a method of scanning a material includes providing a fixture assembly having a top member having a first body with a first plurality of holes; a bottom member having a second body with a second plurality of holes; and an interconnecting member connecting the top member and the second member to provide a gap between the top member and the bottom member, where a hole in the first plurality of holes is aligned with a second hole in the second plurality of holes to form a hole-pair. The method further includes inserting an edge of the material into the gap; and coupling a plurality of sensors into the hole-pair and measuring at least an amplitude of a sound wave through the material.

Other aspects, features, and techniques of the invention will become more apparent from the following description taken in conjunction with the drawings.

BRIEF DESCRIPTION OF THE SEVERAL VIEWS OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which like elements are numbered alike in the several FIGURES:

DETAILED DESCRIPTION OF THE INVENTION

Figure 1:
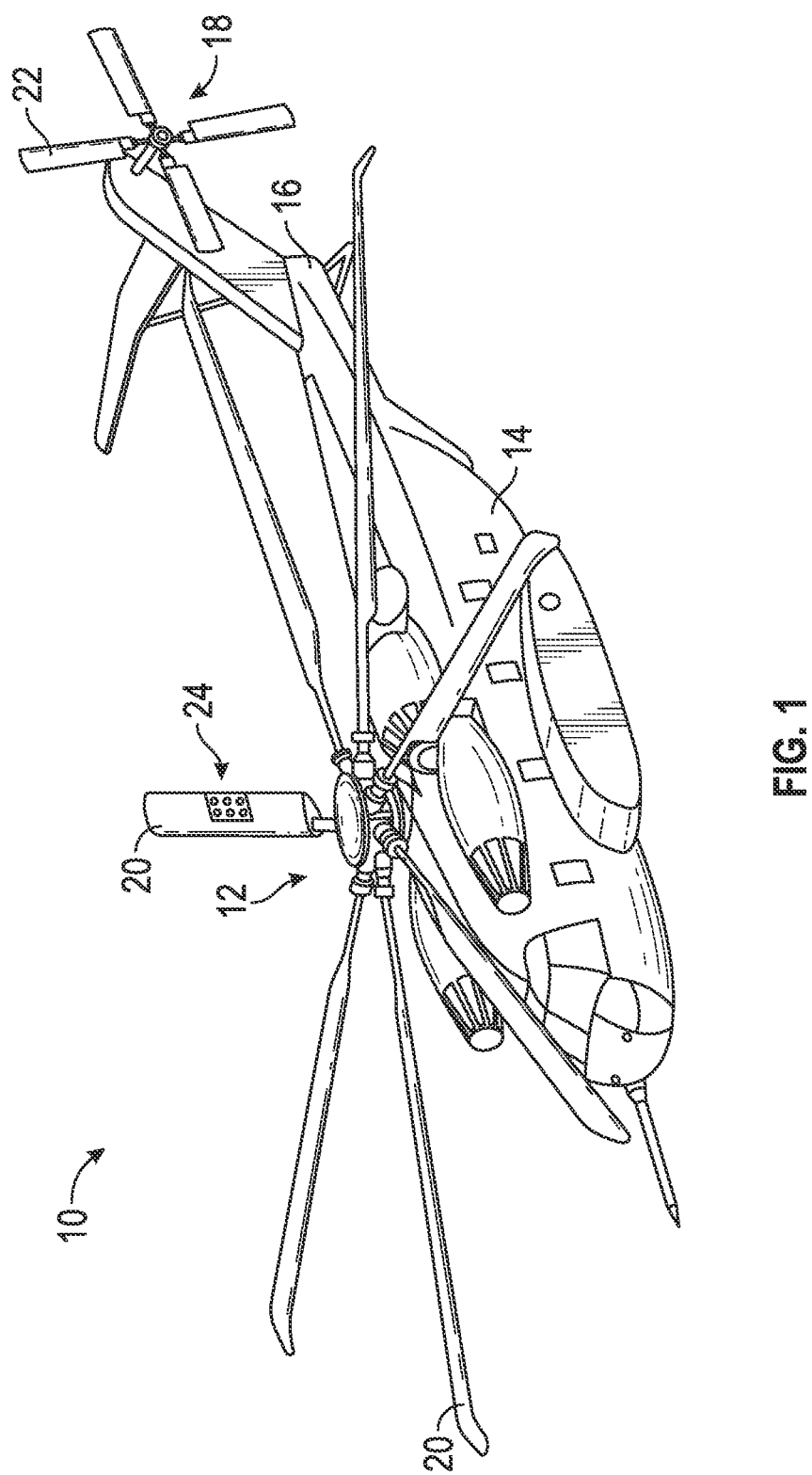
FIG. 1 is a view of an exemplary system according to an embodiment of the invention.

Referring to the drawings, FIG. 1 illustrates a rotary-wing aircraft 10 with an ultrasonic scanning fixture assembly 24 (also referred to as fixture assembly 24) for non-destructive inspection (NDI) of the rotor blades 20 according to an embodiment of the invention. As illustrated, rotary-wing aircraft 10 has a main rotor system 12 and includes an airframe 14 having an extending tail 16 which mounts a tail rotor system 18, such as an anti-torque system. The main rotor system 12 includes a plurality of rotor blades 20 that are driven to rotate about a main rotor hub while the tail rotor system 18 includes a plurality of rotor blades 22 that are driven to rotate about a tail rotor hub.

In embodiments, the rotor blades 20, 22 may be selectively coupled to the fixture assembly 24 during certain aspects of fabrication of the rotor blades 20, 22 from composite prepregs such as, e.g., post autoclave curing. The selective coupling could also be post-fabrication inspection or testing of the rotor blades, such as, e.g., in the field, in order to assess the integrity of the composite rotor blades 20, 22. In an embodiment, the fixture assembly 24 may be selectively coupled to the rotor blades 20, 22 such that a portion of the rotor blade 20 may reside within a gap 46 (See FIG. 2D) in the fixture assembly 24. In an embodiment, the fixture assembly 24 may receive on opposing sides a transmitting and receiving sensor/transducer for detecting defects or delamination during through transmission ultrasonic scanning of the rotor blades 20, 22. In a non-limiting example, the fixture assembly 24 may be coupled to an ultrasonic mobile scanning system with a transmitting transducer for transmitting a high frequency ultrasonic energy through the rotor blade 20 on one side of the blade 20. The sound energy is introduced and propagates through the rotor blade 20 in the form of waves. The propagated wave through the blade 20 is transformed into an electrical signal by a receiving transducer disposed on the other side of the blade 20 and is displayed on a screen for a user. The fixture assembly 24 ensures that the transmitter and receiver are at predetermined locations to ensure that the signal is received consistently.

In an embodiment, the ultrasonic scanning system may be an Olympus Epoch XT portable ultrasonic flaw detector that may utilize a plurality of contact transducers, which are both available from the Olympus Corporation. Although the fixture assembly 24 is illustrated with the use of a rotor blade 20, 22 for through transmission ultrasonic scanning, it is to be understood that the fixture assembly 24 may be utilized on other composite structures where through-transmission ultrasonic inspection is used for detecting defects within the composite structure. For instance, aspects could be used in testing composite rocket engine cases, composite elements of non-rotary aircraft, automotive applications, building structures, non-composite structures or any other structure in which flaw detection is needed. Additionally, while described in terms of an ultrasonic device such as the 5077PR, it is understood that the fixture assembly 24 could be used in other flaw detection devices which use other forms of radiation or sound transmission through a structure.

FIGS. 2A-2D depict an exemplary embodiment of a fixture assembly 24 as used on a rigid structure such as, e.g., a rotor blade 20 according to an embodiment of the invention. As illustrated, fixture assembly 24 includes a top member 30, a bottom member 32, an interconnecting member 34 that interconnects the top member 30 to the bottom member 32, and a plurality of substantially similar wheels 35 coupled to the top member 30 and the bottom member 32. In an embodiment, the top member 30, bottom member 32, interconnecting member 34, and wheels 35 may be made of polyethylene. However, in embodiments, each member 30, 32, 34, and wheels 35 may be made of metal such as aluminum or aluminum alloy, steel, or other similar materials without departing from the scope of the invention. While not required in all aspects, a biasing member such as a spring can be disposed between the top and bottom members 30, 32 so that the top member 30, bottom member 32 can separate to enlarge or reduce the gap 46 to fit component structures with different thicknesses.

Figure 2A:
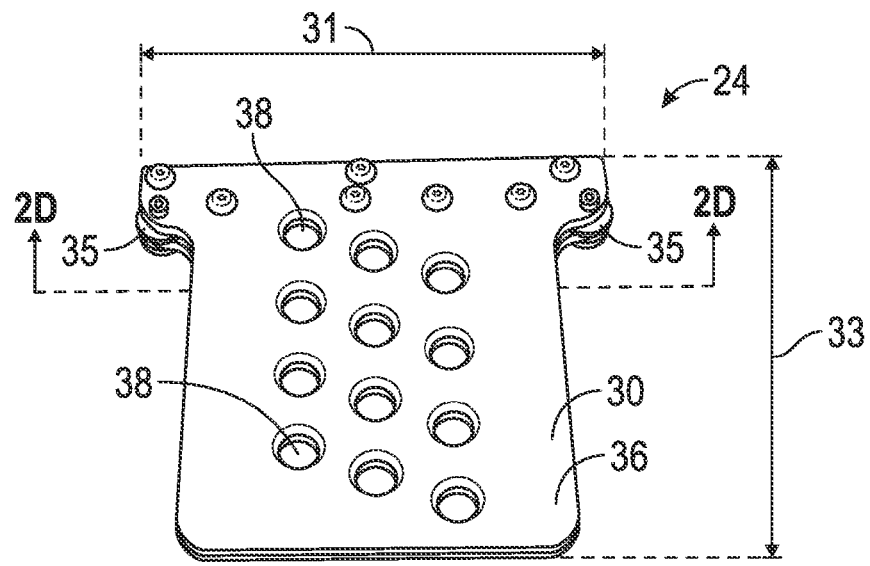
FIG. 2A illustrates a top perspective view of the fixture assembly of FIG. 1 according to an embodiment of the invention.
Figure 2B:
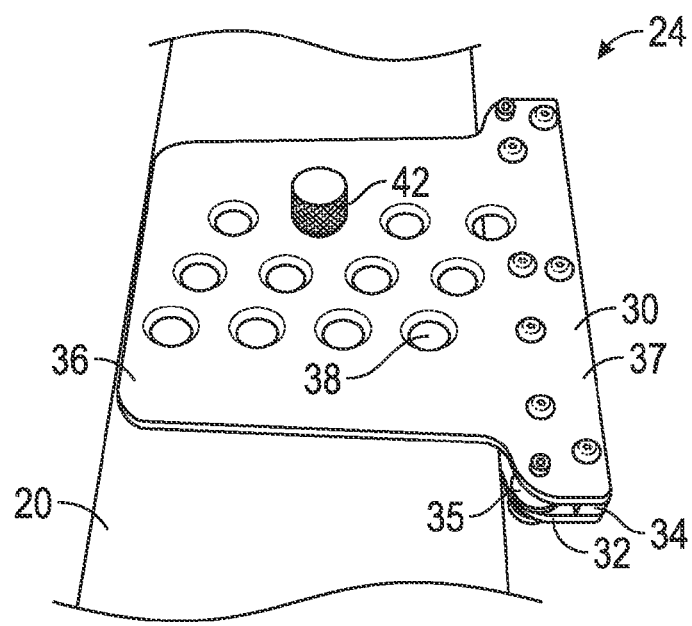
FIG. 2B illustrates a side perspective view of the fixture assembly of FIG. 1 but shown being used with ultrasonic transducers according to an embodiment of the invention.

With particular reference to FIGS. 2A-2B, the top member 30 has a generally rigid body 36 with a longitudinal length 31 and a width 33. Also, the body 36 includes a plurality of substantially similar holes 38 that traverse through the body 36. In an embodiment, each hole 38 has a diameter that is sized to receive a complementary shaped ultrasonic transducer 42. In the example shown, each hole 38 is generally circular in shape and is configured to selectively receive a generally cylindrically-shaped ultrasonic transducer 42 (FIG. 2D) for ultrasonic inspection of the rotor blade 20. In an embodiment, the top member 30 may be generally planar if scanning a generally horizontal composite rotor blade 20 is intended. However, in embodiments, the top member 30 may have other geometries such as, e.g., an arcuate shape, an angular shape, or the like to scan complementary shaped composite structures without departing from the scope of the invention. In an embodiment, the holes 38 may be arranged on body 36 according to a predefined order which reflects a scanning pattern for a particular composite structure being scanned by a user of the fixture assembly 24.

Figure 2C:
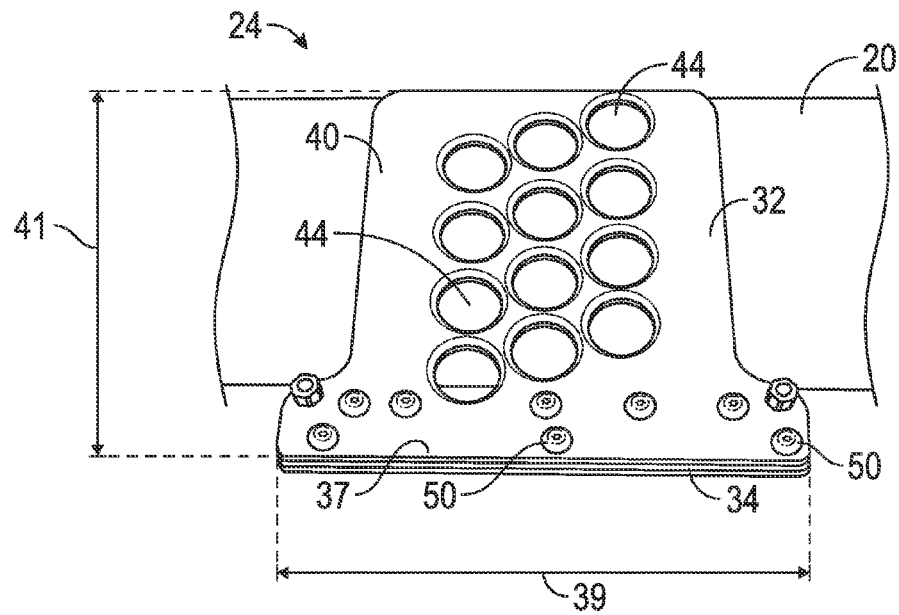
FIG. 2C illustrates a bottom perspective view of the fixture assembly shown in FIG. 1 according to an embodiment of the invention.

Also, with reference to FIG. 2C, the bottom member 32 is substantially similar to the top member 30 (i.e., similar in length, width, and contour) and has a generally rigid body 40 with longitudinal length 39 and a width 41. In an embodiment, the length 39 and width 41 is substantially the same as length 31 and width 33 of top member 30 (See FIG. 2A). Also, body 40 includes a plurality of substantially similar holes 38, 44 that traverse through the body 40. In an embodiment, each hole 38, 44 has a diameter that is sized to receive a complementary shaped ultrasonic transducer 43 (See FIG. 2D). The ultrasonic transducer 43 may be substantially similar in dimensions to the ultrasonic transducer 42 shown and described with reference to FIG. 2B. Also, each hole 38, 44 is generally circular in shape and may selectively receive a conformally shaped ultrasonic transducer for ultrasonic inspection of the rotor blade 20. But, in embodiments, the hole 38, 44 may be sized to have other geometries based on the external dimension of the transducer 42, 43 being used. As illustrated in the figure, the bottom member 32 is generally planar in shape if scanning a generally horizontal composite rotor blade 20 (See FIG. 2B) is intended. However, in embodiments, the bottom member 32 may have other geometries such as, e.g., an arcuate shape, an angular shape, or the like to follow complementary shaped surfaces of composite structures without departing from the scope of the invention. In an embodiment, the holes 44 of the bottom member 32 may be arranged to match the arrangement of holes 38 in the top member 30 so that each hole 38 in the top member 30 is aligned with a respective hole 44 in the bottom member 32 (also referred to as a "hole pair") as will be described in further detail below with reference to FIG. 2D.

Figure 2D:
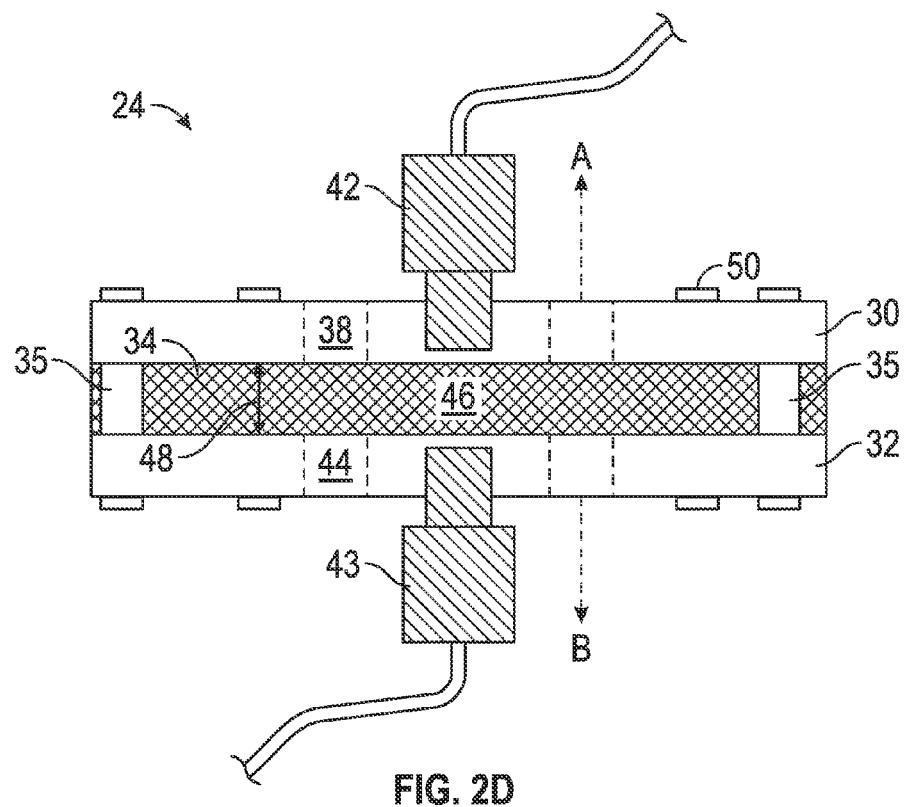
FIG. 2D illustrates a cross-sectional view of the fixture assembly shown in FIG. 2A according to an embodiment of the invention.

Also illustrated in FIGS. 2B-2D, an interconnecting member 34 is selectively and fixedly coupled to both the top member 30 and the bottom member 32 through a plurality of screws 50 near a longitudinal edge 37 of the fixture assembly 24 (corresponding to length 31 and length 39). In an embodiment, the interconnecting member 34 in generally rectangular in shape and may be made from polyethylene. The interconnecting member 34 operates to provide a gap 46 between the top member 30 and the bottom member 32 for receiving, in an example, a chord length of the rotor blade 20 during ultrasonic scanning. In embodiments, the thickness 48 of interconnecting member 34 may be made of a larger or smaller gap 46 in order to be selectively conforming to the thickness of the particular composite structure being inspected. By way of example, member 34 could include a screw which allows manual adjustment of the width of the gap 46 or a spring which automatically widens gap 46 according to the shape of the object/composite structure being measured. Another embodiment may include a U-shaped bridge connecting the top member 30 and bottom member 32. The top and bottom members 30, 32, which may have a single set of aligned holes, are raised or lowered incrementally by the bridge in a direction perpendicular to a line bisecting the front and rear wheels 35. Also, a third wheel and articulated wheels may be included to negotiate a curved radius around an edge of the composite structure. Also, the fixture assembly 24 includes a plurality of substantially similar wheels 35 that are coupled to the top member 30 and the bottom member 32. The wheels 35 are carried within the gap 46 and are held against, and in frictional engagement with either, the leading or trailing edge of the rotor blade 20. The wheels 35 function to guide the fixture assembly 24 spanwise along the rotor blade 20 when a driving force is imparted on the fixture assembly 24 along the spanwise direction while the wheels 35 of the fixture assembly 24 are frictionally engaged with the leading edge or the trailing edge of the rotor blade 20. In this manner, the hole pairs remain at a consistent distance from the edge of the rotor blade 20 while the fixture assembly 24 is moved along the length of the rotor blade 20. While shown as using wheels 35, it is understood that other sliding mechanisms can be used, such as low friction materials which allow the fixture assembly 24 to slide along the edge.

With particular reference to FIG. 2D, the fixture assembly 24 has a plurality of hole pairs in top member 30 and bottom member 32 that are provided to align a transmitting transducer 42 with a receiving transducer 43 during ultrasonic scanning. Particularly, in an example, hole 38 formed in top member 30 (aligned along direction of axis A) is in alignment with a corresponding and a directly opposite hole 44 (aligned along direction of axis B) in bottom member 32. The aligned hole pairs 38, 44 function to align complementary transducers 42, 43 coaxially and reduce or eliminate erroneous readings obtained by the ultrasonic transducers that is frequently associated with misalignment of transducers.

In operation, and with reference to FIG. 1-FIG. 2D, the fixture assembly 24 may be selectively coupled to the rotor blade 20 by inserting, in an example, a leading edge of the rotor blade 20 into the gap 46 along a chord length of the rotor blade 20. The fixture assembly 24 is held against the leading edge of the rotor blade 20 by applying a force that causes the wheels 35 to be in frictional engagement with the leading edge of the rotor blade 20. A single transducer for pulse echo or a plurality of transducers 42, 43 are inserted into a plurality of hole pairs with one transducer 42 in order to conduct a through transmission ultrasonic scan of the rotor blade 20. Particularly, a transmitting transducer such as, e.g., transducer 42 is inserted into hole 38 in top member 30 and a receiver transducer 43 is inserted into a coaxial hole location in the bottom member 32 in order to coaxially align the transducers 42, 43. The ultrasonic scanning is performed by measuring the amplitude of the sound waves as they change in time. Once a reading is obtained, the ultrasonic transducer pairs 42, 43 are moved to another coaxial hole pair and the ultrasonic testing is again performed. Similarly, the fixture assembly 24 is moved spanwise along the rotor blade 20 to a new location on the rotor blade 20 by guiding the leading edge of the blade against the wheels 35. Once a new location is selected, the ultrasonic testing is performed for the hole pairs 38, 44 at the new location. As will be appreciated by those of skill in the art, this through transmission ultrasonic scanning procedure is susceptible to a wide array of alternatives. Thus, it is contemplated that any number of other procedures and practices may likewise be utilized such as, for example, by utilizing an A-scanning methodology or a C-scanning methodology for pulse echo and through transmission ultrasonic scanning The terminology used herein is for the purpose of describing particular embodiments only and is not intended to be limiting of the invention. While the description of the present invention has been presented for purposes of illustration and description, it is not intended to be exhaustive or limited to the invention in the form disclosed. Further, while described in the context of the manufacture of parts for a helicopter, it is understood that aspects can be used in other contexts in which a coating is to be selectively disposed on a surface, such as in semiconductor manufacturing. Many modifications, variations, alterations, substitutions, or equivalent arrangement not hereto described will be apparent to those of ordinary skill in the art without departing from the scope and spirit of the invention. Additionally, while the various embodiment of the invention have been described, it is to be understood that aspects of the invention may include only some of the described embodiments. Accordingly, the invention is not to be seen as limited by the foregoing description, but is only limited by the scope of the appended claims.

What is claimed is:

1. An apparatus for use in scanning a material, comprising:
a top member having a first body with a first plurality of holes;
a bottom member having a second body with a second plurality of holes; and
an interconnecting member connecting the top member and the second member forming a fixture assembly having a gap receptive of the material to be scanned between the top member and the bottom member, the interconnecting member establishing an alignment of the first plurality of holes and the second plurality of holes; and
a plurality of wheels coupled to the top member and the bottom member, the plurality of wheels spanning the gap.

2. The apparatus of claim 1, wherein each of the first plurality of holes is configured to receive a corresponding shaped sensor.

3. The apparatus of claim 1, wherein each of the second plurality of holes is configured to receive a corresponding shaped sensor.

4. The apparatus of claim 1, wherein the interconnecting member is coupled to each of the top member and the bottom member along a longitudinal edge of the apparatus.

5. The apparatus of claim 1, wherein the interconnecting member is coupled to each of the top member and the bottom member with a plurality of screws.

6. The apparatus of claim 1, wherein the plurality of wheels are configured for rotational engagement with an edge of the material.

7. The apparatus of claim 1, wherein the top member is made from a polyethylene or a metal.

8. The apparatus of claim 1, wherein the bottom member is made from a polyethylene or a metal.

9. The apparatus of claim 1, wherein the interconnecting member is made from a polyethylene or a metal.

10. A method of scanning a material, comprising:
providing a fixture assembly comprising:
a top member having a first body with a first plurality of holes;
a bottom member having a second body with a second plurality of holes; and
an interconnecting member connecting the top member and the second member to provide a gap between the top member and the bottom member;
wherein at least one of the first plurality of holes is aligned with at least one of the second plurality of holes to form a hole-pair;
inserting an edge of the material into the gap;
inserting a first sensor in the at least one of the first plurality of holes;
inserting a second sensor in the at least one of the second plurality of holes; and
measuring at least an amplitude of a sound wave passing from one of the first and second sensors to the other of the first and second sensors through the material.

11. The method of claim 10, further comprising:
moving the fixture assembly along a spanwise length of the material to a new scanning location; and
measuring at least the amplitude of a sound wave through the material at the new scanning location.

12. The method of claim 10, wherein the interconnecting member is connected to each of the top member and the bottom member along a longitudinal edge of the fixture assembly.

13. The method of claim 10, wherein the interconnecting member is connected to each of the top member and the bottom member with a plurality of screws.

14. The method of claim 10, wherein a plurality of wheels are coupled to each of the top member and the bottom member.

15. The method of claim 14, wherein the plurality of wheels are in rotational engagement with an edge of the material.

16. The method of claim 10, wherein the top member is made from a polyethylene or a metal.

17. The method of claim 10, wherein the bottom member is made from a polyethylene or a metal.

18. The method of claim 10, wherein the interconnecting member is made from a polyethylene or a metal.

* * * * *